United States Patent
Wise et al.

(10) Patent No.: US 8,677,119 B2
(45) Date of Patent: *Mar. 18, 2014

(54) REMOTE DATA VIEWER

(75) Inventors: Kelly Wise, Villa Park, CA (US);
Meredith Shaebanyan, Anaheim, CA (US)

(73) Assignee: Kelley Wise, Villa Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,672

(22) Filed: May 16, 2012

(65) Prior Publication Data

US 2012/0224754 A1 Sep. 6, 2012

Related U.S. Application Data

(62) Division of application No. 12/723,283, filed on Mar. 12, 2010, now Pat. No. 8,195,937, which is a division of application No. 11/625,072, filed on Jan. 19, 2007, now Pat. No. 7,685,417, which is a division of application No. 10/166,000, filed on Jun. 10, 2002, now Pat. No. 7,181,617.

(51) Int. Cl.
*H04L 29/06* (2006.01)

(52) U.S. Cl.
USPC .......................................................... 713/164

(58) Field of Classification Search
None
See application file for complete search history.

(56) References Cited

U.S. PATENT DOCUMENTS

| | | | |
|---|---|---|---|
| 4,682,869 A | 7/1987 | Itoh et al. | |
| 4,870,497 A | 9/1989 | Chamzas et al. | |
| 4,979,049 A | 12/1990 | Chamzas et al. | |
| 5,189,526 A | 2/1993 | Sasson | |
| 5,204,756 A | 4/1993 | Chevion et al. | |
| 5,432,871 A | 7/1995 | Novik | |
| 6,760,483 B1 * | 7/2004 | Elichai et al. | 382/241 |
| 6,934,698 B2 | 8/2005 | Judd | |
| 2001/0000265 A1 * | 4/2001 | Schreiber et al. | 713/201 |
| 2002/0108050 A1 | 8/2002 | Ralley | |

* cited by examiner

*Primary Examiner* — Brandon Hoffman
(74) *Attorney, Agent, or Firm* — Eric B. Alspaugh, APC

(57) ABSTRACT

A medical image and data application service provider system provides a way of remotely viewing and manipulating medical images and data for diagnostic and visualization purposes by users unconstrained by geography. Medical images and data are stored on one or more servers running application service provider software along with meta-data such as access control information, origin of information and references to related data. A set of medical data consisting related information is sent as an encrypted stream to a viewing station running client software in a secure execution environment that is logically independent of the viewing station's operating system.

21 Claims, 2 Drawing Sheets

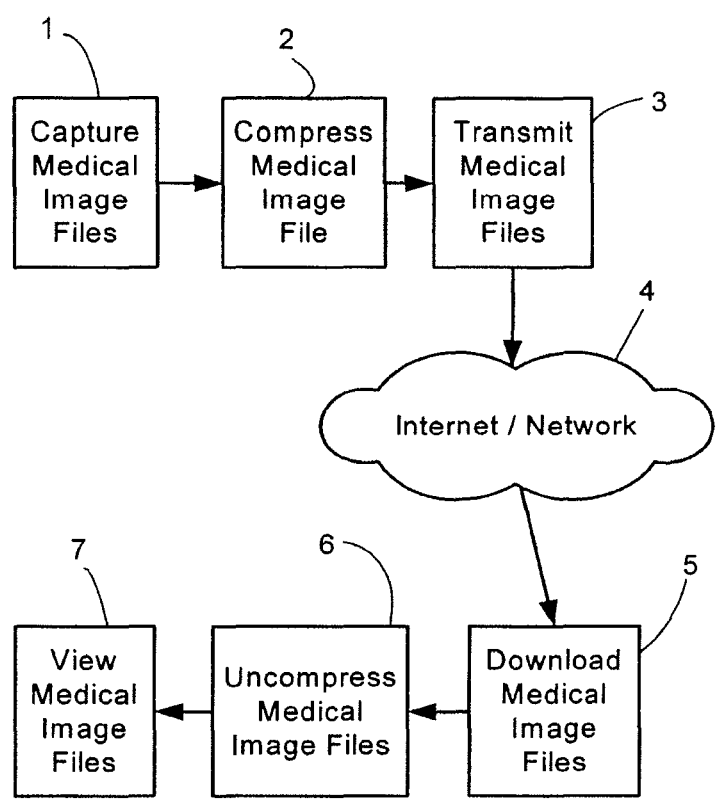
F I G . 1

REMOTE DATA VIEWER

CROSS-REFERENCE TO RELATED APPLICATIONS

This application is a divisional application of U.S. application Ser. No. 12/723,283, filed Mar. 12, 2010, which is a divisional of U.S. application Ser. No. 11/625,072, filed Jan. 19, 2007 and issued as U.S. Pat. No. 7,685,417 on Mar. 23, 2010, which is a divisional of U.S. application Ser. No. 10/166,000, filed Jun. 10, 2002 and issued as U.S. Pat. No. 7,181,617 on Feb. 20, 2007, all of which are incorporated herein by reference.

BACKGROUND

It is very desirable to obtain medical imaging data with CT, MRI, PET, or other diagnostic imaging systems or any type of image capture system and then to permit persons to view remotely all the medical images without having to transmit the actual image files or allow the image files to actually download into the receiving viewing computer. Physicians for example, or other imaging users have a need to quickly access and analyze large numbers of image files from remote image capture systems securely, without downloading or storing the image files onto their computer. Present methods for this all rely on transmitting a medical image file to the viewer which is prohibitively slow and uses too much transmission bandwidth.

A present embodiment of the invention for remote image viewing is U.S. Pat. No. 5,432,714 to Novik; (1995) which discloses a system of compressing and transmitting data to be decompressed and viewed by an experienced or trained viewer, however, for medical diagnostic imaging, this system is unacceptably slow and costly compared to our inventive method and system. Our invention, the Remote Virtual Medical Diagnostic Imaging Viewer, allows a patient or physician or any other user needing secure remote image viewing, to easily view and manipulate the images and files over a wide area network like the Internet, but in a secure execution environment, without downloading the actual image files onto the hard drive of the viewer which is the method of prior art systems.

U.S. Pat. No. 4,682,869 to Itoh et al.; U.S. Pat. Nos. 4,870, 497 and 4,979,049 to Chamzas et al.; U.S. Pat. No. 4,999,715 to Porcellio et al.; U.S. Pat. No. 5,166,987 to Kageyama; U.S. Pat. No. 5,189,526 to Sasson; and U.S. Pat. No. 5,204,756 to Chevion et al. show prior art systems. However, the prior art methods of image data transmission and remote image viewing, particularly when applied to medical diagnostic imaging, do not make use of our novel method of using an image storing application provider server to enable a remote secure executable environment, independent of the operating system of a viewing computer to temporarily reconstruct medical image files, rather than compressing, transmitting and then and uncompres sing the actual medical image files interactively. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

In our study of image data transmission techniques we have identified a need for a system that significantly decreases the time and cost of viewing images remotely for medical diagnostic analysis. Since accurate reproduction of an entire medical image file with all of the rest of the captured frames of image data is very necessary for medical diagnostic purposes. Our inventive method is unique because by it's nature, it is secure, saves time, is loss-less, and provides all the medical images available on the server to be viewed interactively, not just a few of the images as with prior art systems. Instead of lossy compression and file transmission systems described in prior art, our inventive method preserves remotely viewed image data in a secure environment.

With our inventive method, the image files are never actually downloaded onto the remote viewer. The remote viewer only displays an exact representation of the actual file stored on the application server. Images can be viewed over a wide area network like the Internet by logging into our website and using our invention.

SUMMARY OF THE INVENTION

In the preferred embodiment of the invention, one or more servers with medical image files stored on them, run application service provider software and send streams of medical data and images, to temporarily reconstruct and manipulate the image files remotely in a secure execution environment on an authorized user's personal computer.

In the existing embodiment of the invention a computer or other capture device, captures a lossy image file then compresses and transmits the compressed image file which is then downloaded onto a computer hard drive and decompressed by the remote receiver for viewing. In contrast, the preferred embodiment of the invention does not require transmitting the actual medical image files to a receiver and is therefore a more efficient method of remote medical image viewing.

Besides the objectives and advantages of the preferred embodiment of the invention described above, there are objectives and advantages also which are:
 a) to lower the cost and provide high security or regulatory compliance with the need for remote viewing of medical images and data for medical diagnostics and any other field requiring secure remote viewing of image files and data.
 b) to provide a faster way to view digital images remotely
 c) To view and manipulate all image files without compressing, uncompressing, and downloading the files into a hard drive or opening the actual patient image file on the remote server.
 d) To be able to use a digital imaging viewer without having to buy and install medical imaging or any other viewing or compression/decompression software.
 e) To be able to see large numbers of images in sequence animated in rapid succession and manipulate them remotely faster than existing methods.
 f) To provide physicians a more efficient method of using diagnostic images to plan a surgery
 g) To create incentives for physicians to refer patients to radiologists or medical diagnostic imaging providers.

These objects described above and others are achieved in the preferred embodiment of the invention and allow for further advantages to become apparent from a consideration of the ensuing description and drawings.

BRIEF DESCRIPTION OF THE DRAWING

The drawings shown are two flowcharts, which are
FIG. 1, representing the present invention and showing the steps of image data acquisition, compression and transmission of the image files for remote viewing. The second drawing.

REFERENCE NUMERALS IN DRAWINGS: FIGS. 1-2

Figure 2:
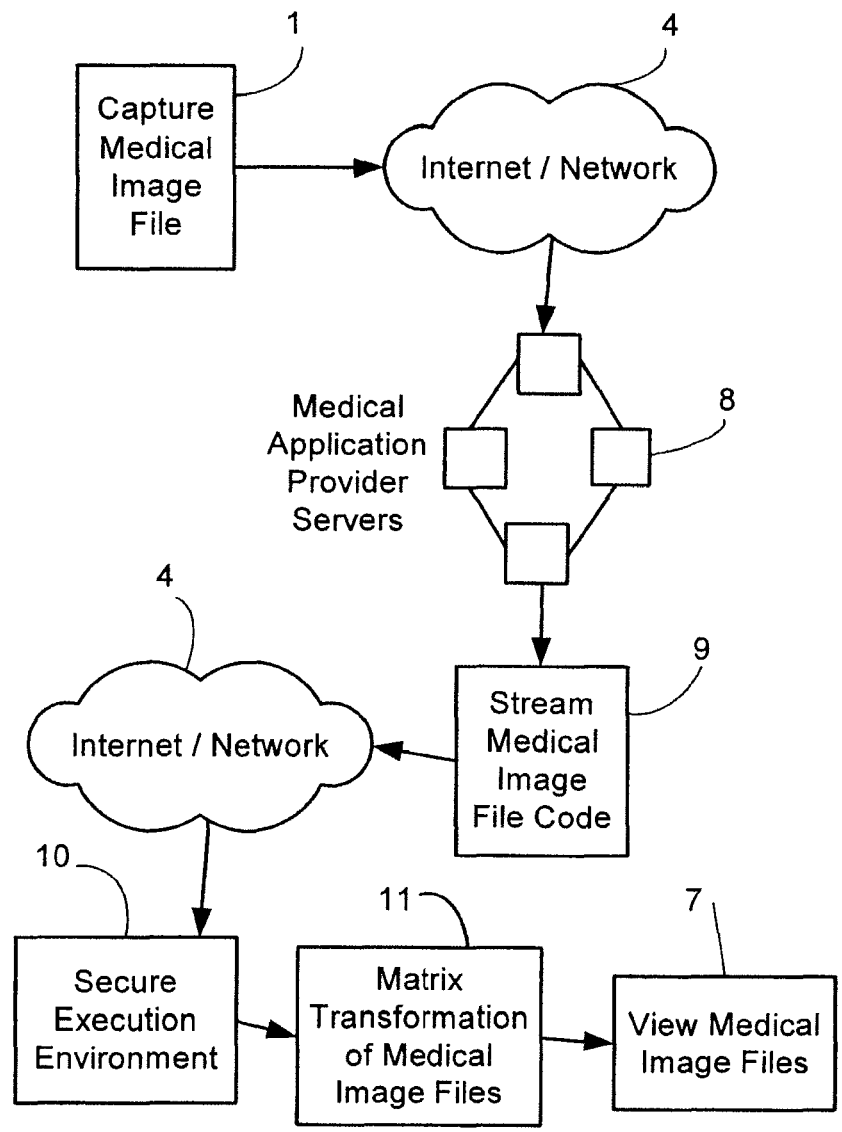
FIG. 2 represents the preferred embodiment of the present invention showing the steps of sending streams of encoded data to be reconstructed for viewing in a remote secure executing environment.

1. capture device or server
2. compression of medical image files
3. transmitting compressed medical image files
4. the Internet or a network
5. downloading medical image files to a hard drive
6. uncompressing medical image files
7. view medical image files
8. image storing medical application service provider servers
9. streaming an encrypted medical image file in a Boolean code
10. the streamed medical image data is accessed and unencrypted in the secure execution environment running on the remote viewing computer
11. matrix transformation is applied to the reconstructed image files to allow for remote manipulation of the reconstructed medical images

DETAILED DESCRIPTION

The present invention describes an apparatus for capturing and transmitting the image file for remote viewing interactively. The invention will be described in FIG. 1, which is a block diagram schematic of one preferred embodiment of the present invention. Medical image files are captured (1) and then compressed (2) transmitted (3) over a network or the Internet (4) which are downloaded on a users computer (5) and uncompressed (6) and viewed remotely (7).

FIG. 2 is a flowchart of the preferred operation of the present invention, and will be explained with reference to the apparatus of FIG. 1, although other appropriate apparatus may be substituted in performing the inventive method. In this method for viewing a file remotely, the medical image files are first captured (1) transmitted (3) over a network or the Internet (4) to one or more servers running application service provider software (8) which are stored with meta data including access control information, origin of the data, and references to related data. This data is encrypted and streamed (9) out on a network or the Internet (4). The encrypted medical image data streams are decrypted by software running in a secure execution environment (10), and can be remotely manipulated by real time matrix transformation of the reconstructed medical image files (11) viewed and analyzed remotely (7).

This preferred embodiment of the present invention as shown in FIG. 2 is thusly shown to be an improved method over the present invention offering a simpler and less costly secure method for remote viewing and analysis of large medical imaging files.

What is claimed is:

1. A method of a user operating an electronic device configured to receive data from a source external to the device, comprising:
   receiving the data into a buffer of the electronic device;
   applying a function to the data within the buffer under (a) partial control of the user and (b) partial control of an external server; and
   rendering to the user a result of applying the function to the data.

2. The method of claim 1, wherein the step of receiving the data into the buffer comprises operating a virtual machine on the electronic device.

3. The method of claim 1, wherein the buffer comprises operating a virtual machine.

4. The method of claim 1, further comprising accessing the data through a website.

5. The method of claim 1, wherein the function comprises a matrix transformation.

6. The method of claim 5, wherein the step of applying a matrix transformation to the data comprises operating a virtual machine on the electronic device.

7. The method of claim 1, wherein the function comprises a diagnostic function.

8. The method of claim 1, wherein the function comprises an analyzing function.

9. The method of claim 1, wherein the function comprises a visualization function.

10. The method of claim 1, wherein the function comprises an interactive viewing function.

11. The method of claim 1, wherein the function comprises decoding.

12. The method of claim 1, wherein the function comprises reconstructing an image.

13. The method of claim 1, wherein the function comprises uncompressing.

14. The method of claim 1, wherein the buffer operates within a secure execution environment that prohibits the user from maintaining a copy of the data.

15. The method of claim 1, wherein the electronic device is running an operating system, and the buffer operates within a secure execution environment that is logically independent of the operating system.

16. The method of claim 1, further comprising receiving the data in a streaming format.

17. The method of claim 1, further comprising receiving the data in an encrypted format.

18. The method of claim 1, further comprising receiving the data comprises an image.

19. The method of claim 1, further comprising receiving the data comprises video information.

20. The method of claim 1, further comprising receiving the data comprises metadata.

21. The method of claim 1, further comprising receiving the data comprises an animation.

* * * * *